United States Patent
Sato et al.

(10) Patent No.: US 8,647,275 B2
(45) Date of Patent: Feb. 11, 2014

(54) ULTRASOUND DIAGNOSIS APPARATUS AND PROGRAM

(75) Inventors: Takeshi Sato, Nasushiobara (JP); Ryota Osumi, Nasushiobara (JP); Tomohisa Imamura, Nasushiobara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 1235 days.

(21) Appl. No.: 12/237,809

(22) Filed: Sep. 25, 2008

(65) Prior Publication Data

US 2009/0088638 A1 Apr. 2, 2009

(30) Foreign Application Priority Data

Sep. 28, 2007 (JP) ................................ 2007-256338

(51) Int. Cl.
*A61B 8/06* (2006.01)
*G06K 9/40* (2006.01)
*G06T 5/00* (2006.01)

(52) U.S. Cl.
USPC ........................................................ 600/443

(58) Field of Classification Search
None
See application file for complete search history.

(56) References Cited

U.S. PATENT DOCUMENTS

| | | | |
|---|---|---|---|
| 5,619,998 A * | 4/1997 | Abdel-Malek et al. | 600/437 |
| 6,042,545 A * | 3/2000 | Hossack et al. | 600/443 |
| 6,511,426 B1 * | 1/2003 | Hossack et al. | 600/437 |
| 7,087,022 B2 * | 8/2006 | Chalana et al. | 600/449 |
| 7,693,563 B2 * | 4/2010 | Suresh et al. | 600/407 |
| 8,150,151 B2 * | 4/2012 | Gori et al. | 382/166 |
| 2003/0167003 A1 * | 9/2003 | Masotti et al. | 600/437 |
| 2005/0053305 A1 * | 3/2005 | Li et al. | 382/260 |
| 2005/0277835 A1 * | 12/2005 | Angelsen et al. | 600/437 |
| 2006/0084869 A1 | 4/2006 | Kim et al. | |
| 2007/0083114 A1 * | 4/2007 | Yang et al. | 600/437 |

FOREIGN PATENT DOCUMENTS

| | | |
|---|---|---|
| EP | 1 739 623 A1 | 1/2007 |
| JP | 8-280688 | 10/1996 |
| JP | 2005-296331 | 10/2005 |

OTHER PUBLICATIONS

U.S. Appl. No. 12/540,584, filed Aug. 13, 2009, Osumi.

* cited by examiner

*Primary Examiner* — Long V. Le
*Assistant Examiner* — Lawrence Laryea
(74) *Attorney, Agent, or Firm* — Oblon, Spivak, McClelland, Maier & Neustadt, L.L.P.

(57) ABSTRACT

An ultrasound diagnosis apparatus includes an image synthesizing unit for performing the following processings. That is, the image synthesizing unit performs a multiple resolution analysis for the respective images of a plurality of frames by a predetermined transform processing, performs a filter operation processing for each of the coefficients corresponding among the images of a plurality of frames, in each coefficient of each resolution obtained by the multiple resolution analysis, and performs an inverse transform processing of the predetermined transform processing for a result of the filter operation processing to generate an image of one frame.

14 Claims, 11 Drawing Sheets

ULTRASOUND DIAGNOSIS APPARATUS AND PROGRAM

CROSS-REFERENCE TO RELATED APPLICATIONS

This application is based upon and claims the benefit of priority from prior Japanese Patent Application No. 2007-256338, filed Sep. 28, 2007, the entire contents of which are incorporated herein by reference.

BACKGROUND OF THE INVENTION

1. Field of the Invention

The present invention relates to an ultrasound diagnosis apparatus and an ultrasound diagnosis program, and more in particular, to an ultrasound diagnosis apparatus and an ultrasound diagnosis program to synthesize images of a plurality of frames obtained by ultrasound scan.

2. Description of the Related Art

An ultrasound diagnosis apparatus is a device that ultrasound generated from a piezoelectric vibrator embedded in an ultrasound probe is radiated to a subject and a reflected signal generated by a difference of acoustic impedance of tissues of the subject is received by the piezoelectric vibrator for display. According to the ultrasound diagnosis apparatus, image data can be obtained easily in real time from simple manipulation performed by only touch of the ultrasound probe to a body surface. Therefore, the ultrasound diagnosis apparatus is widely used for diagnosis of a function of an internal organ and a shape thereof.

An ultrasound diagnosis method, which obtains information for a living body by a reflected wave from tissues of or blood cells of a subject, has been rapidly developed by two great techniques such as an ultrasound pulse reflecting method and an ultrasound Doppler method. B mode image data and color Doppler image data obtained by use of such techniques are indispensable for an ultrasound diagnosis these days.

Meanwhile, in a case of the ultrasound image data obtained by the ultrasound diagnosis apparatus, a particle type noise (so-called, a speckle noise) occurs by random interference of reflected ultrasound from a plurality of reflectors in a subject. Such speckle noise is known as an obstacle of the ultrasound diagnosis together with system noise of the ultrasound diagnosis apparatus.

As a method of reducing the speckle noise, there is, for example, a compound scan method. The compound scan method is divided into a spatial compound scan and a frequency compound scan.

The spatial compound scan is a technique that transmission and reception of ultrasound is performed for the same portion of a subject from a plurality of different directions, to sum and synthesize a plurality of obtained image data, thereby generating image data for display. On the other hand, the frequency compound scan is a technique that a plurality of image data is collected using different ultrasound frequencies for the same portion of a subject, to sum and synthesize the collected image data, thereby generating image data for display.

As a technique for a synthesis processing of image data as above, a following technique is disclosed in, for example, Japanese Unexamined Patent Application Publication No. H8-280688. In Japanese Unexamined Patent Application Publication No. H8-280688, a method of generating a composite ultrasound image including: dividing individually consecutive image frames into a plurality of sub-image areas to estimate and evaluate a local movement vector of the sub-image area; estimating and evaluating an overall image movement based on the estimated and evaluated local movement vector; and displaying a composite XFOV image based the estimated and evaluated overall image movement, is disclosed.

According to the method disclosed in Japanese Unexamined Patent Application Publication No. H8-280688, a large composite ultrasound image can be generated, which is displayed as an image of an enlarged viewing angle (XFOV).

In addition, as a method of reducing the speckle noise, a following technique is disclosed in, for example, Japanese Unexamined Patent Application Publication No. 2005-296331. That is, in Japanese Unexamined Patent Application Publication No. 2005-296331, there is disclosed a ultrasound diagnosis apparatus including: image data generating means for performing a transmission and reception of ultrasound from a plurality of directions of a subject to generate image data; wavelet transform means for performing a wavelet transform for the image data to calculate a low frequency wavelet transform coefficient and a plurality of high frequency wavelet transform coefficients for each resolution level; edge information detecting means for detecting edge information for the image data based on the high frequency wavelet transform coefficients; coefficient processing means for operating a weighting of the high frequency wavelet transform coefficients based on the detected edge information; wavelet inverse-transform means for generating edge-emphasized image data by a wavelet inverse-transform using the weighting-operated high frequency wavelet transform coefficients; and display means for displaying the edge-emphasized image data.

According to the ultrasound diagnosis device disclosed in Japanese Unexamined Patent Application Publication No. 2005-296331, it becomes possible to effectively reduce a speckle noise and to emphasize an edge in ultrasound image data.

Upon display of a tissue image with an ultrasound diagnosis apparatus, as synthesizing methods at the time of synthesizing and displaying image data obtained by an ultrasound scan, there are mainly three following methods known.

(Synthesizing Method 1) Spatial Compound Scan

In a case of the spatial compound scan, as shown in FIG. 8, an ultrasound probe 101 is fixed and held to perform a scan from different directions each frame. When the ultrasound scan is performed from different directions as above, and since interference conditions are different even in an echo from the same place, correlation with a speckle becomes less. Therefore, a mean value operation or a maximum value operation is performed for an overlap region (an overlap region 107 of a first scan image 103 and a second scan image 105), to reduce a speckle.

In addition, a tissue border which is vertical to an ultrasound beam generates a clearer border echo by specular reflection. With this, the irradiation of the ultrasound beam from multiple directions enables echoes from a tissue border at various angles to be displayed clearly.

(Synthesizing Method 2) Panoramic View

The panoramic view is an image method as such disclosed in Japanese Unexamined Patent Application Publication No. H8-280688, which is a technique for displaying a wider viewing angle that, as shown in FIG. 9, an ultrasound probe 101 moves towards a section of a scan and the movement of the ultrasound probe 101 is detected from the obtained image data, to adjust a position by translational movement and rotational movement of the image data for a synthesis processing. Currently, a synthesis processing of overwriting the latest image on a previous image is generally performed.

(Synthesizing Method 3) Combination Focus

The combination focus is a technique that, as shown in FIG. 10, transmission and reception of ultrasound beam is performed multiple times changing a transmission focus from the same direction not from different directions, to synthesize images obtained by the transmission and reception. That is, in the combination focus, an image 111A of a short-distance region is obtained by an ultrasound beam 111 of a short-distance focus and an image 113A of a long-distance region is obtained by an ultrasound beam 113 of a long-distance focus, to synthesize the obtained images.

However, the above-described methods of synthesizing image data have the respective problems as follows.

First, in the case of the spatial compound scan, upon synthesizing the image data, as shown in FIG. 8, an overlap region 107 and non-overlap regions 109 are generated between image data (the first scan image 103 and the second scan image 105) related to the corresponding synthesizing. In this case, for the non-overlap regions 109, the image data related to the corresponding synthesizing is displayed as it is. On the other hand, for the overlap region 107, an image synthesis processing is performed by an image synthesizing method such as a mean value operation or a maximum value operation or the like.

Herein, if employing the maximum value operation as the image synthesizing method, a border between the overlap region 107 and the non-overlap regions 109 is displayed naturally. However, when an artifact having a higher gray scale is present in one image data, the artifact is displayed as it is. Meanwhile, if employing the mean value operation as the image synthesizing method, the border between the overlap region 107 and the non-overlap regions 109 is displayed unnaturally. Even in any cases, that is, even if employing the maximum value operation or the mean value operation as the image synthesizing method, there is a problem in that the image data after the corresponding synthesis processing looks somewhat blurred to the viewer.

In addition, in the case of using the panoramic view, when the overlap region is generated, the overwriting processing is performed for the image data of the corresponding region as described above. Thus, a blurring of the image due to the synthesis processing does not occur. However, notwithstanding the presence of the image data in the overlap region, it cannot be said that unuse of the image data sufficiently enjoys a merit according to the synthesis processing of the image data. In other words, use of the image data in the overlap region can obtain the same effect as the above-described spatial compound scan. However, since it has the same problem as the spatial compound scan at the same time, the problem which the spatial compound scan has is required to be solved, whatever it takes.

In addition, like the use of the panoramic view for example, the image data obtained by the scan from different positions has a clear region and a blurred region in the corresponding image data due to a position where each image data is obtained.

For example, as shown in FIG. 11, for a first image 133 where a blurred region is present in the right of a region of interest 131 and a second image 135 where a blurred region is present in the left of the region of interest 131, the mean value operation or the maximum value operation is carried out to perform a synthesis processing, and this leads to obtaining only an image data where the blurred region is enlarged.

Therefore, in this case, it is preferable to obtain the image data 137 with the clear regions only by use of only the clear region for the synthesis processing, not by use of the blurred regions present in the image data related to the corresponding synthesis processing. However, currently, a technique for performing such synthesis processing automatically is not disclosed.

In the case of using the combination focus, and since the combination focus divides the image data for synthesizing, it has a problem that a border is visible on the image data after the corresponding synthesis processing. A method to sum weights varying a little is considered, but a synthesis processing method to contribute to increasing a resolving power is more preferable than the method to sum varying weights.

Of course, the techniques disclosed in Japanese Unexamined Patent Application Publication No. H8-280688 and Japanese Unexamined Patent Application Publication No. 2005-296331 do not solve the problems described with reference to FIGS. 8 to 11.

BRIEF SUMMARY OF THE INVENTION

The present invention is directed to solve such problems and objects of the present invention is to provide an ultrasound image diagnosis apparatus and an ultrasound diagnosis program to realize that, in image data created by a synthesis processing, a border of an overlap region and a non-overlap region between image data related to the corresponding synthesis processing is not visible discontinuously, an artifact of a high intensity is not emphasized visually, and, even though a blurred region is included in the image data related to the corresponding synthesis processing, a blurred region resulting therefrom is not generated.

In order to accomplish such objects, an ultrasound diagnosis apparatus according to the first aspect of the present invention is characterized in performing an ultrasound scan multiple times such that the same region of a subject overlaps in at least a portion and generating images of a plurality of frames based on a received echo, which includes: an analyzing unit configured to perform a multiple resolution analysis for the respective images of a plurality of frames by a predetermined transform processing; a filter operation processing unit configured to perform a filter operation processing for each of the coefficients corresponding among the images of a plurality of frames, in each coefficient of each resolution obtained by the multiple resolution analysis by the analyzing unit; and an image generating unit configured to perform an inverse transform processing of the predetermined transform processing for a result of the filter operation processing by the filter operation processing unit, to generate an image of one frame.

In order to accomplish such subject, a program according to the second aspect of the present invention is characterized in enabling a computer to function as an ultrasound diagnosis apparatus for performing an ultrasound scan multiple times such that the same region of a subject overlaps in at least a portion and for generating images of a plurality of frames based on a received echo, which, in the computer, realizes: an analyzing function configured to perform a multiple resolution analysis for the respective images of a plurality of frames by a predetermined transform processing; a filter operation function configured to perform a filter operation processing for each of the coefficients corresponding among the images of a plurality of frames, in each coefficient of each resolution obtained by the multiple resolution analysis by the analyzing function; and an image generating function configured to perform an inverse transform processing of the predetermined transform processing for a result of the filter operation processing by the filter operation processing function, to generate an image of one frame.

According to the present invention, it is possible to provide an ultrasound image diagnosis apparatus and an ultrasound diagnosis program to realize that, in image data created by a synthesis processing, a border of an overlap region and a non-overlap region between image data related to the corresponding synthesis processing is not visible discontinuously, an artifact of a high intensity is not emphasized visually, and, even though a blurred region is included in the image data related to the corresponding synthesis processing, a blurred region resulting therefrom is not generated.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principle of the invention.

DETAILED DESCRIPTION OF THE INVENTION

Hereinafter, an embodiment of the present invention will be described with reference to the accompanying drawings.

Figure 1:
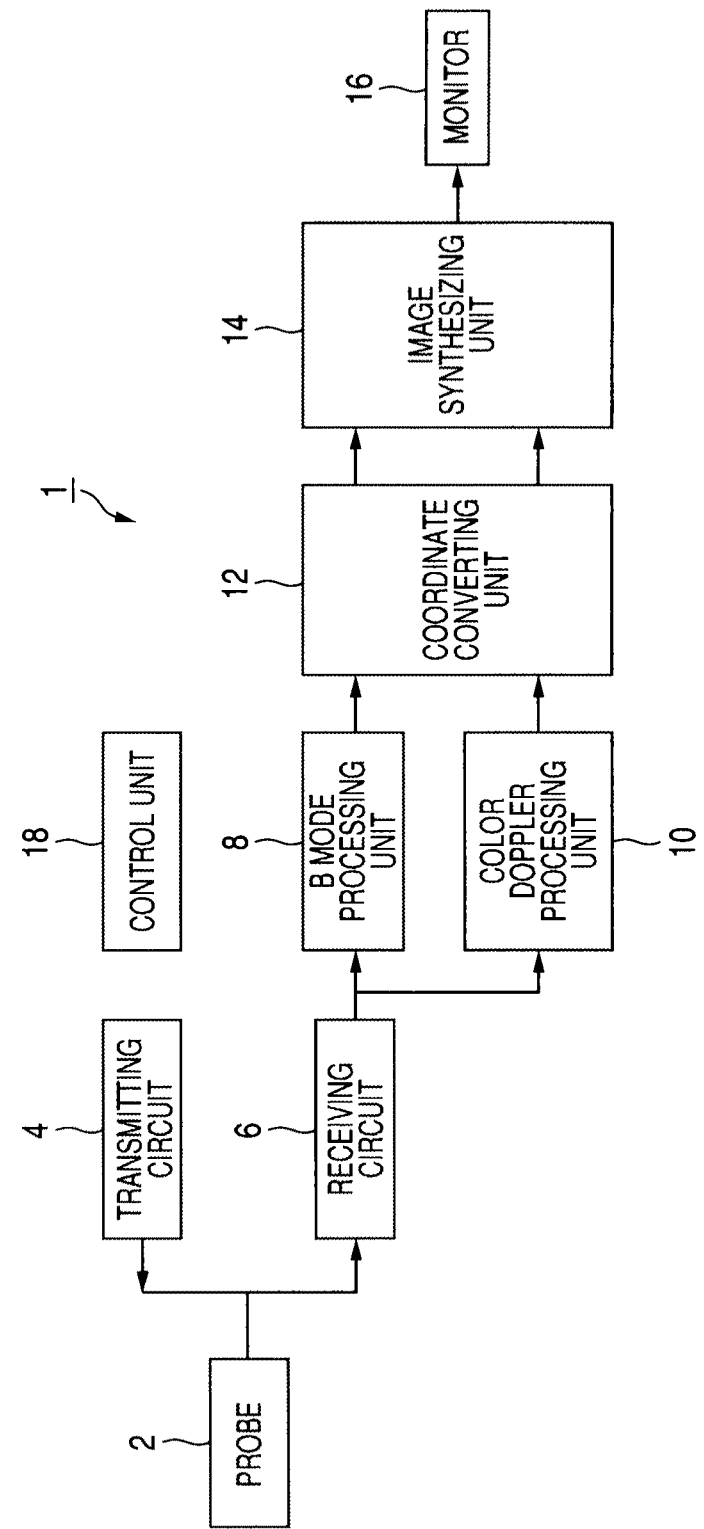
FIG. 1 is a diagram to illustrate an exemplary configuration of an ultrasound diagnosis apparatus related to a one embodiment of the present invention.

FIG. 1 is a diagram to illustrate an exemplary configuration of an ultrasound diagnosis apparatus related to an embodiment of the present invention. As shown in FIG. 1, the ultrasound diagnosis apparatus 1 according to the embodiment includes an ultrasound probe 2, a transmitting circuit 4, a receiving circuit 6, a B mode processing unit 8, a color Doppler processing unit 10, a coordinate converting unit 12, an image synthesizing unit 14, a monitor 16 and a control unit 18.

The ultrasound probe 2 is a device (probe) in charge of transmitting and receiving an ultrasound signal irradiated/reflected to/from a subject and is made of a piezoelectric device such as a piezoelectric ceramic or the like which is a electrically/mechanically reversible transform device. The ultrasound probe 2 is configured of a phased array type whose front end is equipped with a plurality of piezoelectric devices arranged in an array form. With this, the ultrasound probe 2 converts a supplied pulse driving voltage into an ultrasound pulse signal to transmit it to a desired direction in a scan region of the subject and converts the ultrasound signal reflected from the subject into an echo signal corresponding thereto.

The transmitting circuit 4 transmits a driving signal to each piezoelectric device of the ultrasound probe 2, based on a control signal from the control unit 18 at the timing when each transmission channel is given a predetermined transmission delay time. With this, the ultrasound signal is transmitted from each piezoelectric device of the ultrasound probe 2 to the inner side of the subject.

The receiving circuit 6 receives an ultrasound echo signal which is reflected from a mismatching surface of acoustic impedance in the subject according to the transmitting of the ultrasound signal and includes a component and so on scattered by scatters in a tissue, as the echo signal of a voltage amount corresponding to the associated signal through each piezoelectric device of the ultrasound probe 2. The receiving circuit 6 performs a reception delay and a sum processing for the echo signal to generate a receiving signal for output to the B mode processing unit 8 and the color Doppler processing unit 10, respectively.

The B mode processing unit 8 performs an envelope detection for the output signal from the receiving circuit 6 and outputs the detected signal which is in charge of shape information for tissues of the subject, to the coordinate converting unit 12.

The color Doppler processing unit 10 frequency-analyzes speed information based on the output signal from the receiving circuit 6 and outputs the analyzed result which is in charge of moving speed information for the bloodstream and the tissue in the subject, to the coordinate converting unit 12.

The coordinate converting unit 12 coordinate-converts the output signals from the B mode processing unit 8 and the color Doppler processing unit 10 into a display coordinate for output to the image synthesizing unit 14.

The image synthesizing unit 14 receives the signal from the coordinate converting unit 12 and performs various image processings and synthesis processings (described in detail later) about a B mode image and a CFM (color, flow and mapping) image by control of the control unit 18. In addition, the image synthesizing unit 14 performs various quantitative analyses or measurements based on such images, to perform image processings of adding information indicating a result thereof on the image or the like and to convert an image signal obtained by such image processings into a scan signal for TV for output to the monitor 16.

The control unit 18 has a function as a computer including a CPU (processor), memories (RAM/ROM), a hard disk device, a driving device for driving removable media (CD-ROM, FLOPPY (registered trademark) disk, memory card and so on) and the other peripheral devices coupled to internal buses (not shown). The control device 18 controls an entire operation of the ultrasound diagnosis apparatus 1 according to a pre-programmed order upon diagnosis.

An ultrasound image (includes various image about the B mode image and the CFM image, or information for the measurement and the analyzed result) is displayed on the monitor 16 by the above-described configuration.

In addition, typically, in the spatial compound scan, directions (angle) of scan are varied tilted by the ultrasound probe 2 every frame. However, varying the scan every frame is only applied to the B mode image and the same scan every frame is applied to the CFM image. That is, herein, the spatial compound scan and the synthesis processing are performed for only the B mode image. Hereinafter, only a processing of the B mode image will now be described in detail.

Hereinafter, a synthesis processing by means of the image synthesizing unit 14 which is one of main characteristics of the ultrasound diagnosis apparatus 1 related to the first embodiment, will be described in detail.

Figure 2:
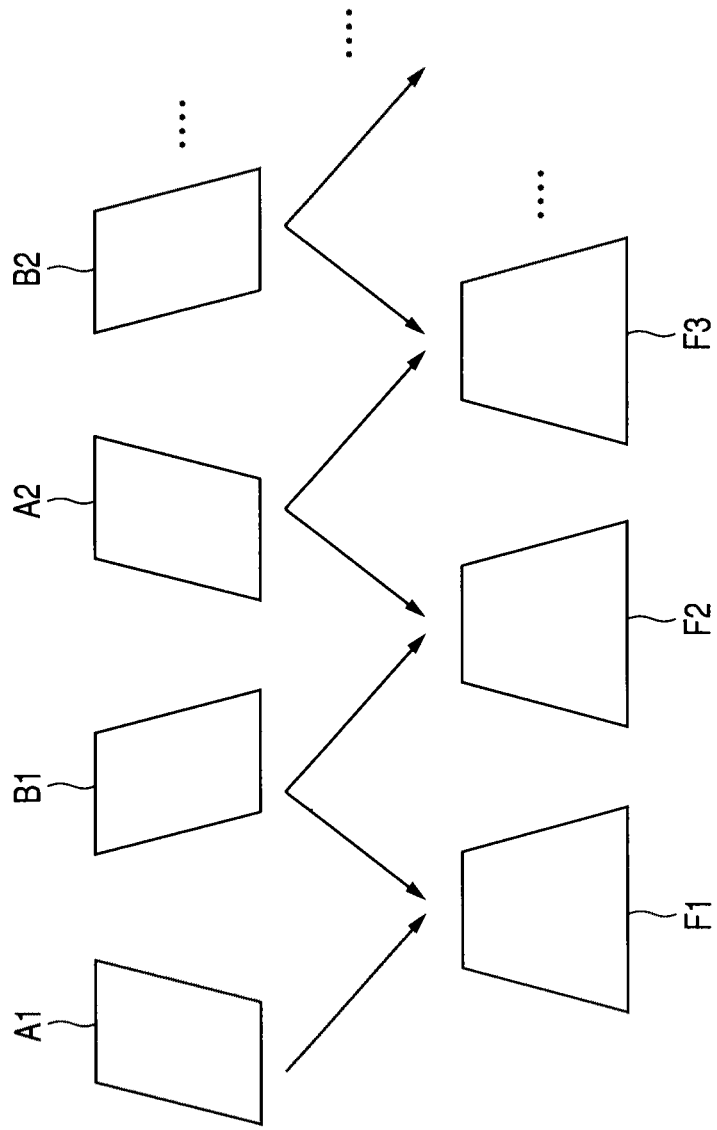
FIG. 2 is a diagram to illustrate an input and an output of an image synthesizing unit.

First, a relation of input and output for a synthesis processing by the image synthesizing unit 14 is one as shown in FIG. 2, for example. That is, images are synthesized by an operation of N frames (or N frames more) to output image data of the same number of frames as the input. More in detail, as shown in FIG. 2, the image data A1 and the image data B1 are synthesized to generate the image data F1, the image data B1 and the image data A2 are synthesized to generate the image data F2, and the image data A2 and the image data B2 are synthesized to generate the image data F3.

In addition, although the example shown in FIG. 2 is an example of performing a two-directional compound processing, an N-directional compound processing may be performed by the ultrasound diagnosis apparatus related to the embodiment.

Figure 3:
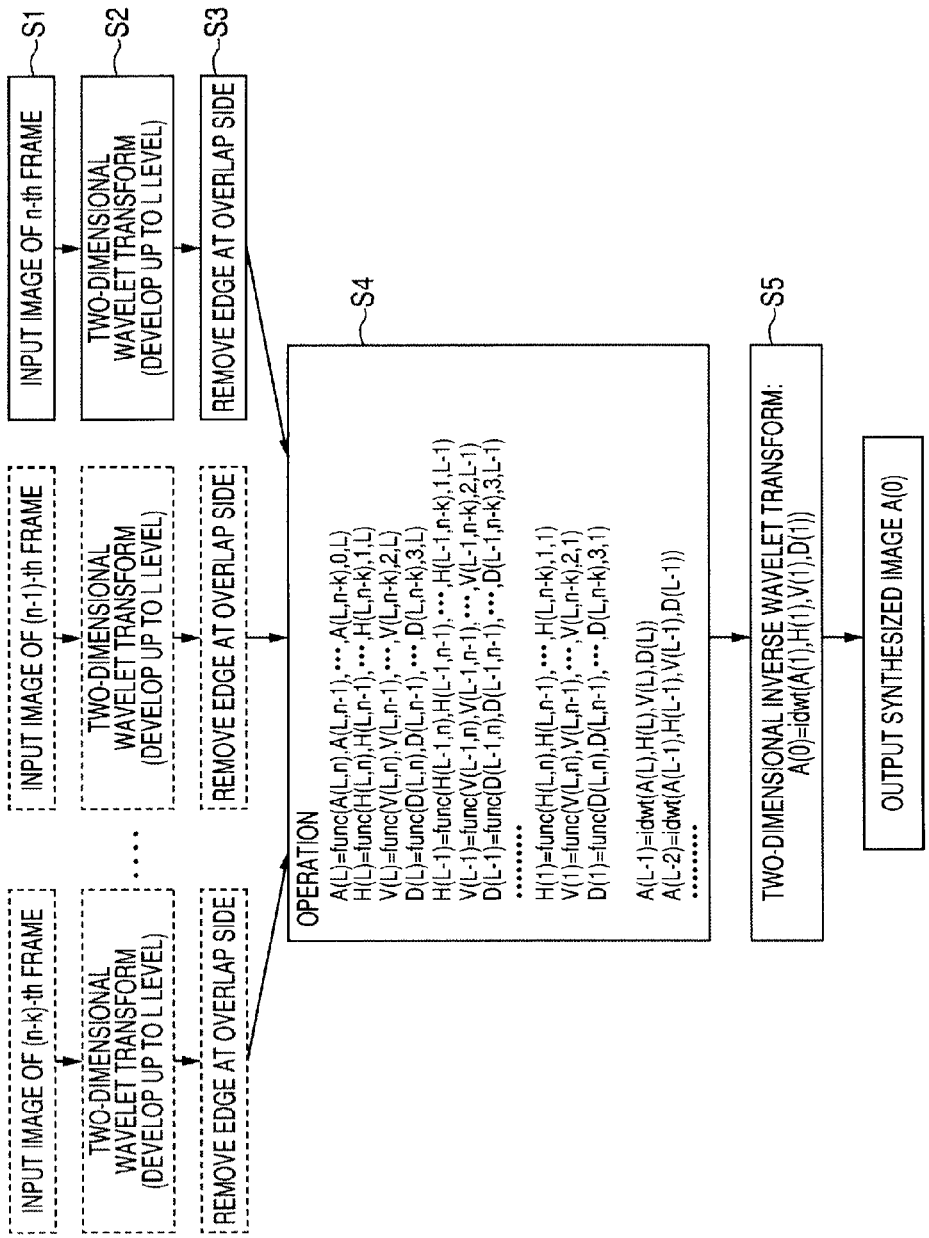
FIG. 3 is a flowchart of a synthesis processing of image data by the image synthesizing unit.

Subsequently, a flow of the synthesis processing by the image synthesizing unit 14 will be described with reference to the flowchart shown in FIG. 3. Herein, a case of the synthesis processing of the image data with (k+1) frames will be described as an example. In addition, processings at the respective steps will be described later with reference to FIG. 4.

First, if the latest image data (an image of the n-th frame) inputs (step S1), the image synthesizing unit 14 performs a discrete two-dimensional wavelet transform of an L level (step S2).

Successively, the image synthesizing unit 14 removes an edge region including edge components present in an overlap region between images related to the synthesis processing (step S3). Typically, upon performing the wavelet transform, the edge components are generated in a high frequency side at the edge of the image. In the image after the synthesis processing, the edge of the image is not an edge any more at present. Therefore, the edge components are unnecessary at the edge thereof. For this reason, the removal of the edge components is performed at the step S3.

Then, the image synthesizing unit 14 performs a predetermined operation processing described later (a processing of performing an operation for each of the wavelet coefficients of frames of (k+1)) (step S4) and performs a two-dimensional discrete inverse wavelet transform for the result of the operation processing (step S5) to obtain the image data A(0) after the synthesis processing.

Hereinafter, a principle of the synthesis processing for the image data in this embodiment will be described with reference to FIG. 4. In this case, a case of the synthesis processing of two images such as an image a and an image b will be described as an example. In detail, the image synthesizing unit 14 performs a multiple resolution analysis (herein, a two-dimensional discrete wavelet transform of a level 2) of the image a and the image b as follows (step S2).

The image synthesizing unit 14 first divides the image a and the image b into wavelet coefficients such as A1 (Approximation), H1 (Horizontal detail), V1 (Vertical detail) and D1 (Diagonal detail) by the two-dimensional discrete wavelet transform of a level 1. Subsequently, it further performs the two-dimensional discrete wavelet transform for the A1 only. With this, A2, H2, V2 and D2 are obtained as shown in FIG. 4. Such processing is performed for both of the image a and the image b.

Figure 4:
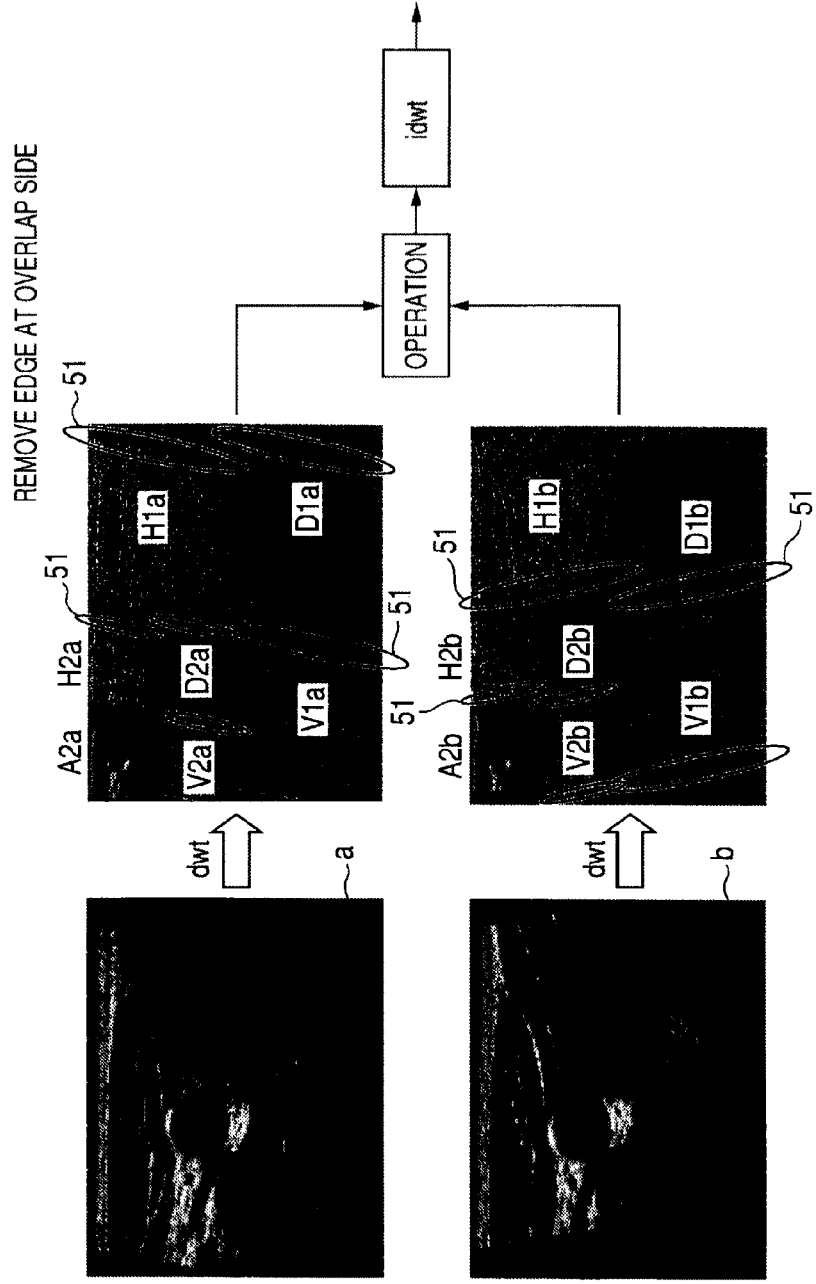
FIG. 4 is a diagram to illustrate a principle of the synthesis processing of the image data in the one embodiment of the present invention.

Then, a processing for removing edge regions represented by surrounding an oval 51 shown in FIG. 4 (for taking a coefficient of a high frequency side of the corresponding edge regions as 0) is performed (step S3).

Such edge region is an edge region which will not be an edge of an image after the synthesis processing. In other words, such edge region is an edge of the corresponding image in a certain one image before the synthesis processing, but is not an edge of the image after the synthesis processing. In addition, this region is a known area before the corresponding synthesis processing. Likewise, in a case of performing the wavelet transform, a region in a range which the edge of the image influences is also a known region before the corresponding synthesis processing.

According to the processings at the steps S1 to S3 described above, the same result can be naturally obtained from the same image. Thus, the current result is reserved one by one, and thus values of the two-dimensional discrete wavelet transform from the (n−k)-th frame to the (n−1)-th frame represented by a broken line in FIG. 3 can be obtained without operation every time again.

The operation processing at the step S4 and the two-dimensional discrete inverse wavelet transform at the steps S5 are processings to perform, for example, the following operation.

In this case, an operational function is represented as func (a1, a2, . . . , aN, M, Level) and the discrete two-dimensional inverse wavelet transform is represented as idwt2. However, a1, a2, . . . , aN represent input data, M=0 represents Approximation, M=1 represents Horizontal detail, M=2 represents Vertical detail, M=3 represents Diagonal detail, and Level represents a wavelet development number.

$A(L)=\text{func}(A(L,n),A(L,n-1)), \ldots ,A(L,n-k),0,L)$ $H(L)=\text{func}(H(L,n),H(L,n-1)), \ldots ,H(L,n-k),1,L)$ $V(L)=\text{func}(V(L,n),V(L,n-1)), \ldots ,V(L,n-k),2,L)$ $D(L)=\text{func}(D(L,n),D(L,n-1)), \ldots ,D(L,n-k),3,L)$ $H(L-1)=\text{func}(H(L-1,n),H(L-1,n-1)), \ldots ,H(L-1,n-k),1,L-1)$ $V(L-1)=\text{func}(V(L-1,n),V(L-1,n-1)), \ldots ,V(L-1,n-k),2,L-1)$ $D(L-1)=\text{func}((D-1,n),D(L-1,n-1)), \ldots ,D(L-1,n-k),3,L-1)$ $H(1)=\text{func}(H(L,n),H(L,n-1)), \ldots ,H(L,n-k),1,1)$ $V(1)=\text{func}(V(L,n),V(L,n-1)), \ldots ,V(L,n-k),2,1)$ $D(1)=\text{func}(D(L,n),D(L,n-1)), \ldots ,D(L,n-k),3,1)$ $A(L-1)=idwt2(A(L),H(L),V(L),D(L))$ $A(L-2)=idwt2(A(L-1),H(L-1),V(L-1),D(L-1))$ $A(0)=idwt2(A(1),H(1),V(1),D(1))$ In this case, A(0) is image data created finally by the synthesis processing.

In addition, an example of the above-described operational function is as follows. For all of the levels, $$\text{func}(a1,a2,\ldots,aN,M,\text{Level})=\text{Mean}(a1,a2,\ldots,aN)$$
$$M=0$$

$$\text{func}(a1,a2,\ldots,aN,M,\text{Level})=\text{AbsMax}(a1,a2,\ldots,aN) M=1,2,3$$

Only, Mean(a, b) is an operation to calculate a mean value of a and b; however, if a=C, a value of b is outputted, and if b=0, a value of a is outputted. Further, AbsMax(a, b) is an operation to output a larger absolute value of a and b.

In addition, more in detail, at the step S4, for example, the following operation is performed.

$$A2=\text{Mean}(A2a,A2b)$$

$$H2=\text{AbsMax}(H2a,H2b)$$

$$V2=\text{AbsMax}(V2a,V2b)$$

$$D2=\text{AbsMax}(D2a,D2b)$$

$$H1=\text{AbsMax}(H1a,H1b)$$

$$V1=\text{AbsMax}(V1a,V1b)$$

$$D1=\text{AbsMax}(D1a,D1b)$$

After performing the above-described operation, the image synthesizing unit 14 performs the two-dimensional discrete inverse wavelet transform for the coefficients A2, H2, V2 and D2 to calculate A1 and performs the two-dimensional discrete inverse wavelet transform for A1, H1, V1 and D1 (step S5) to obtain A(0) which is image data after the synthesis processing.

Hereinafter, effects able to be obtained by the operation processing at the step S4 will be described.

First, performing the mean value operation for the coefficient of the Approximation can obtain an effect that a mean intensity is not varied and an effect that an approximate structure of an image is represented as a mean value between the respective images related to the synthesis processing.

Performing the maximum value operation for the detail coefficients of the H, V and D selects an image having the maximal resolving power of the respective images related to the image processing and automatically selects an image having the maximal resolving power for each pixel. Therefore, taken as a whole, even an overlap border is not visible but is visible as a natural overlap, so an image having the maximal resolving power of the overlap images is displayed for each pixel. Therefore, an effect that the resolving power is increased visually can be obtained.

In other words, objects can be accomplished that a border of an overlap region and a non-overlap region between image data is not visible discontinuously, an artifact of a high intensity is not emphasized visually, and, even though a blurred region is included in the image data, a blurred region resulting therefrom is not generated.

By such operation, clearness of an image by specular reflection expected by the compound scan is accomplished. In this case, in order to obtain an effect of removing speckles additionally, an image processing technique which is referred to as a wavelet shrinkage is used together with the above-described wavelet transform. Since a detail coefficient of a low level is a noise in many cases, the wavelet shrinkage is performed to remove or reduce the speckles.

The func function in a case where such processing is performed is as follows, for example.

$$\text{func}(a1,a2,\ldots,aN,M,\text{Level})=\text{AbsMax}(a1,a2,\ldots,aN)*c(M,\text{Level}) M=1,2,3$$

where, c(M, Level) represents a weight of a wavelet coefficient, for example, takes a value close to 0 if the level is as small as 1 and takes a value close to 1 if the level is large. Values of c(M, Level) may be varied depending on Horizontal, Vertical and Diagonal designated by M. Furthermore, values of c(M, Level) may be 1 or more so as to emphasize an edge at an edge and so on of a tissue.

Figure 5:
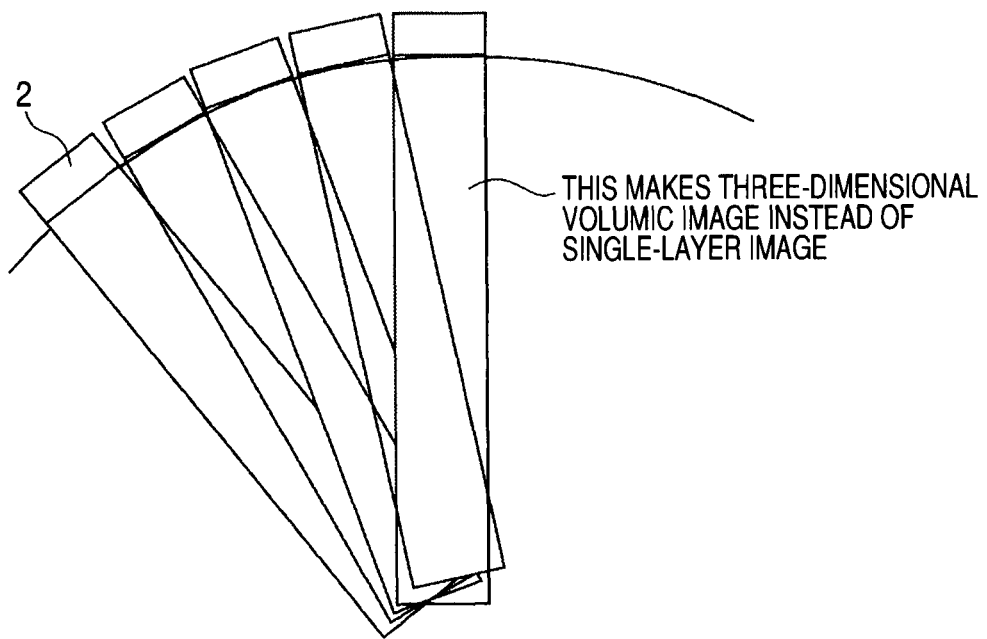
FIG. 5 is a diagram to illustrate a conception of a three-dimensional scan.

The processing by the image synthesizing unit 14 described above is applicable to image data obtained by a plurality of three-dimensional scans which overlap one another as shown in FIG. 5.

FIG. 5 is a diagram to illustrate a figure to move the ultrasound probe 2 while three-dimensional scanning or to observe the same tissue from other windows, that is, a figure to release the ultrasound probe 2 from the subject once and replace the ultrasound probe 2 to the different position of the subject to obtain images repeatedly.

According to such method, the three-dimensional scan is performed for the same region of the subject from different directions multiple times to calibrate locations of the scan-obtained images three-dimensionally, thereby possibly obtaining completely the same sections or data of the same voxels. In this case, a plurality of voxel data are present in the same region, and the synthesis processing is performed for the plurality of voxel data or a plurality of clipped two-dimensional image data. In a case of employing such method as well, it is of course that the above-described synthesis processing by the image synthesizing unit 14 is applicable.

Herein, to make a series of the synthesis processings by the image synthesizing unit 14 described above a program, or to read out the program from a storage medium after programming facilitates sale and distribution thereof as a single software product independent from the ultrasound diagnosis apparatus 1 and enables the techniques related to this embodiment to be used on other hardware.

As described above, according to this embodiment, in the image data created by the synthesis processing, it is possible to provide an ultrasound image diagnosis apparatus and an ultrasound diagnosis program to realize that a border of an overlap region data and a non-overlap region between image data related to the corresponding synthesis processing is not visible discontinuously, an artifact of a high intensity is not emphasized visually, and, even though a blurred region is included in the image data related to the corresponding synthesis processing, a blurred region resulting therefrom is not generated.

In the image data obtained by the synthesis processing by the image synthesizing unit 14 described above, a border of an overlap region and a non-overlap region between image data before the corresponding synthesis processing is natural and moreover the resolving power is increased. The reason why the resolving power is increases is that, since the image data after the corresponding synthesis processing has the largest frequency component of the high frequency components of the image data before the synthesis processing, the synthesis processing is performed in the highest resolution state.

As above, although the present invention has been described based on one embodiment, the present invention is not limited to the above-described embodiment, but various modifications and applications are possible within the gist of the present invention.

First Modified Example

An operational method in the synthesis processing may take, for example, a method of using the Mean operation in all cases or a method of using the AbsMax operation in all cases, in addition to the above-described operational methods.

The method of using the Mean operation in all cases is a processing basically equivalent to a processing of taking just the MAX without performing the wavelet transform. However, in the present one embodiment, since the removal processing of the edge region at the overlap side on the wavelet coefficients is performed as described above, the border at the overlap region is not visible discontinuously.

The method of using the AbsMax operation in all cases is different from the processing of taking just the MAX without performing the wavelet transform and outputs an image having the maximal resolving power for each pixel. However, a mean intensity is sometimes increased or an artifact of a high intensity sometimes remains.

Second Modified Example

Although the synthesis processing has been performed by use of only the coefficients for each pixel in the operational method of the synthesis processing described above, a synthesis processing may be performed by use of coefficients of peripheral pixels of the corresponding pixel.

For example, as a calculating method by the AbsMax for positions (x, y) of two images, a mean value a1 for peripheral 5×5 points including the position (x, y) of the first image is calculated and a mean value a2 for peripheral 5×5 points including the position (x, y) of the second image is calculated, to take a larger absolute value of a1 and a2 as an output value for the position (x, y). Such processing can reduce noises emphasized visually.

Third Modified Example

In the operational method of the synthesis processing described above, the discrete wavelet transform is used for the multiple resolution analysis. In a general discrete wavelet transform, an LPF (Low Pass Filter) and an HPF (High Pass Filter) are multiplied to the corresponding image data and then outputs therefrom are down sampled to a half, respectively. With this, an information amount before transform and after transform is not varied.

However, if performing the inverse wavelet transform after processing the coefficients by use of the wavelet shrinkage, an artifact of a block shape is sometimes visible. In order to prevent it, for example, a stationary wavelet transform may be performed instead of the discrete wavelet transform.

A down sampling is not performed in the stationary wavelet transform. Thus, an information amount becomes four times by transform of one time in a case of processing a two-dimensional image. However, an effect can be obtained that the above-described artifact of a block shape is not visible on the corresponding image even in case of performing the inverse wavelet transform after performing the wavelet shrinkage.

Fourth Modified Example

In the operational method of the synthesis processing described above, the discrete wavelet transform is used for the multiple resolution analysis. However, instead of using the wavelet transform for the multiple resolution analysis, for example, various pyramid transforms such as a Laplacian pyramid, RoL (Ratio of Low pass) pyramid or a Gradient pyramid may be used.

A difference between the wavelet transform and the pyramid transform is that the wavelet transform is an orthogonal transform whereas the pyramid transform is not necessarily an orthogonal transform. However, both of the wavelet transform and the pyramid transform are common in that the multiple resolution analysis is possible thereby.

Fifth Modified Example

Figure 6:
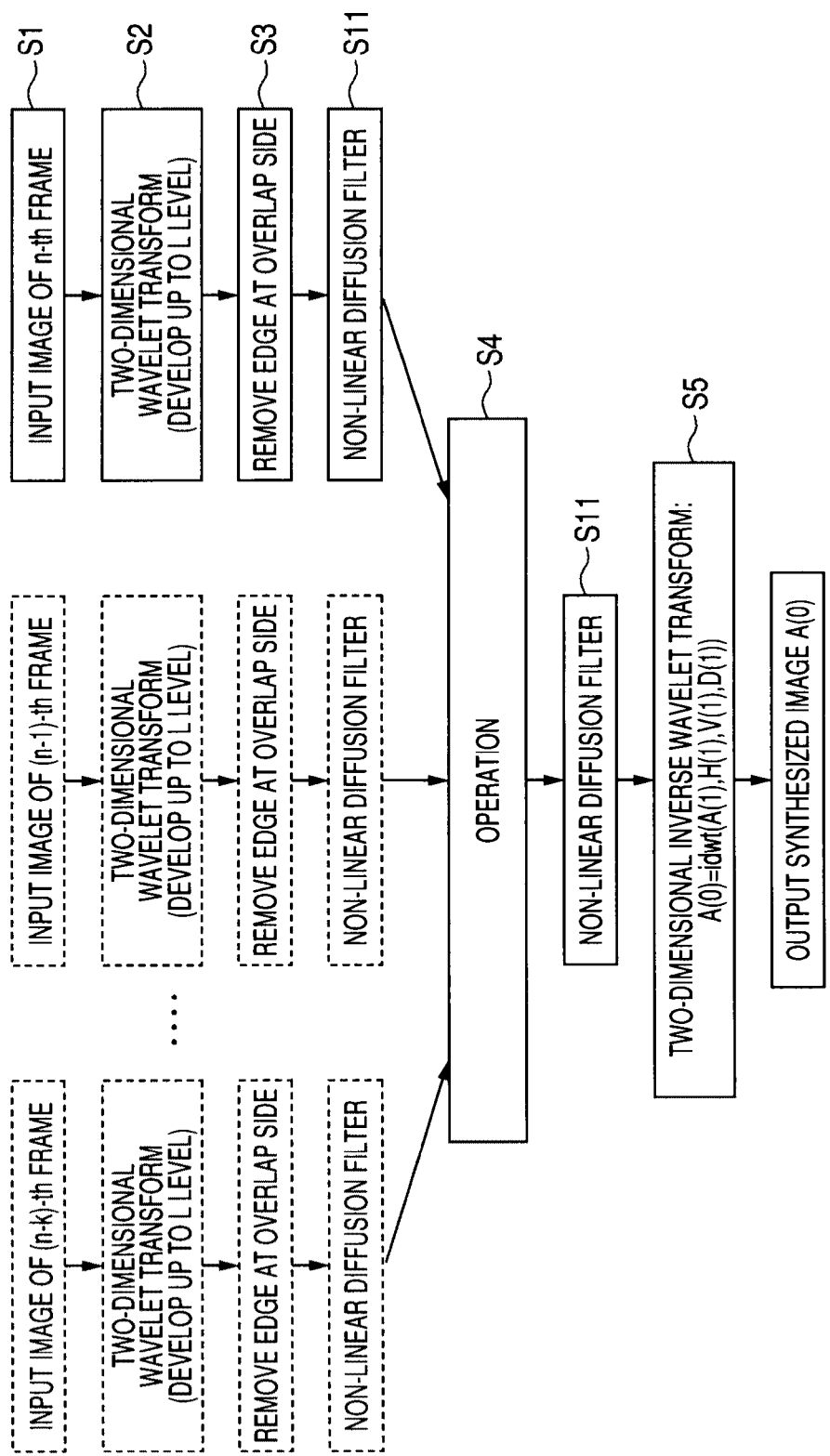
FIG. 6 is a flowchart of a synthesis processing of the image data by the image synthesizing unit in a case of inserting a filtering processing for reduction of speckle or emphasis of edge.

As shown in FIG. 6, a non-linear diffusion filter processing for reducing speckles or emphasizing edges (step S11) may be inserted into any one or both of before the operation processing at the step S4 and after the operation processing at the step S4. For convenience of explanation, the non-linear diffusion filter processing (step S11) is shown inserted into both of before and after the step S4 in FIG. 6.

For example, as disclosed in Japanese Unexamined Patent Application Publication No. 2006-116307, a combined processing of the multiple resolution analysis and the non-linear diffusion filter is inserted before the synthesis processing, to obtain an easily visible synthesized image where the speckles are little and the edges are emphasized. In a case of performing such processing, since the multiple resolution analysis has been performed already, the time taken to perform the multiple resolution analysis can be saved.

Sixth Modified Example

Although a case of using the compound scan is considered in the above-described examples, not limited to the compound scan, the one embodiment is also applicable to a case of moving the ultrasound probe 2 or observing the same tissue from other windows, while performing the panoramic view or the three-dimensional scan.

In addition, in a case of the panoramic view, a motion amount is required to be estimated from an image for translational movement and/or rotational movement of the corresponding image. The details thereof are disclosed in Japanese Unexamined Patent Application Publication No. H8-280688. In a case of performing the three-dimensional scan from different directions as well, a section can be fit to a desired section by three-dimensional translational movement and/or rotational movement. After matching the sections as above, the synthesis processing for the images described in the one embodiment can be performed.

Seventh Modified Example

The one embodiment is applicable to the synthesis processing by the combination focus method. In this case, a border of images related to the synthesis processing overlaps to perform the synthesis processing by the image synthesizing unit 14 described in the one embodiment.

Figure 7:
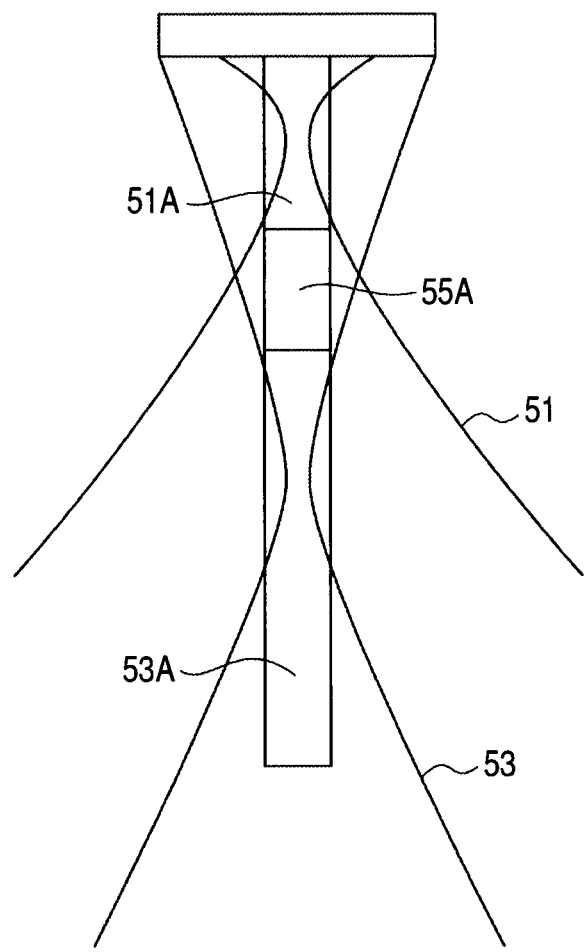
FIG. 7 is a diagram to illustrate a conception of a two-stage combination focus method.
Figure 8:
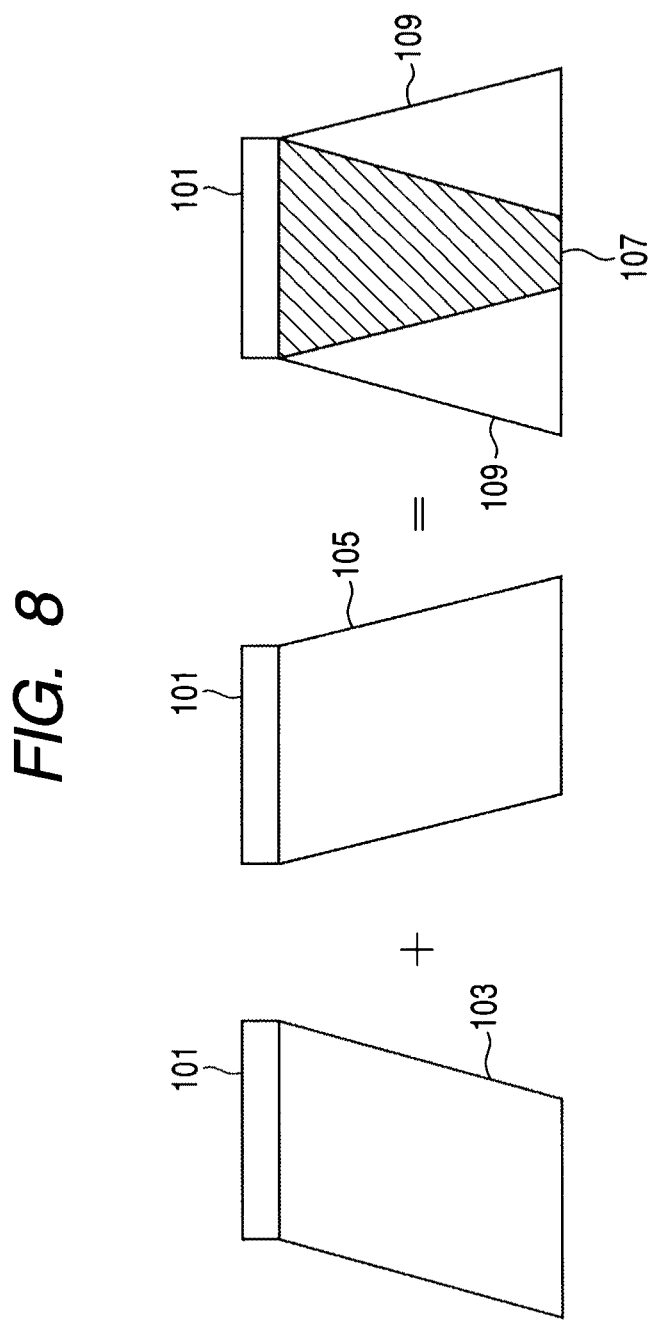
FIG. 8 is a diagram to illustrate a conception of a spatial compound scan.
Figure 9:
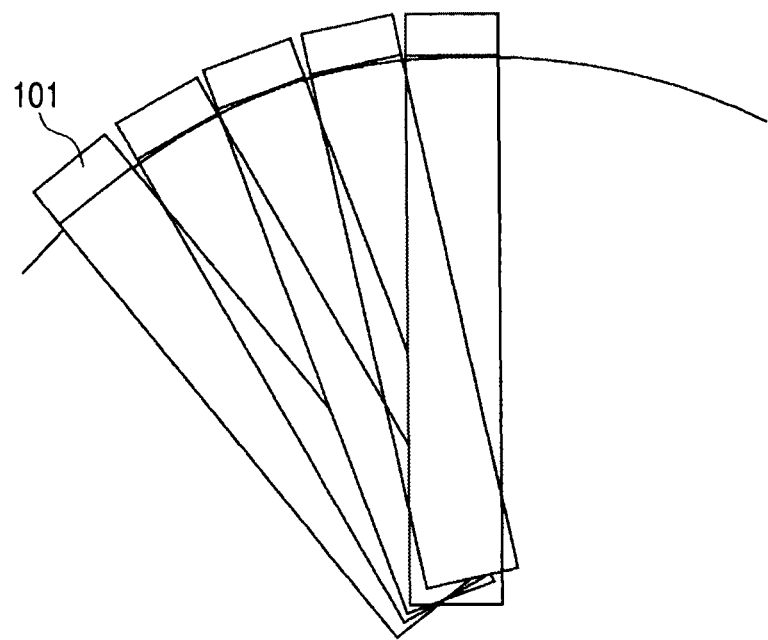
FIG. 9 is a diagram to illustrate a conception of a panoramic view.
Figure 10:
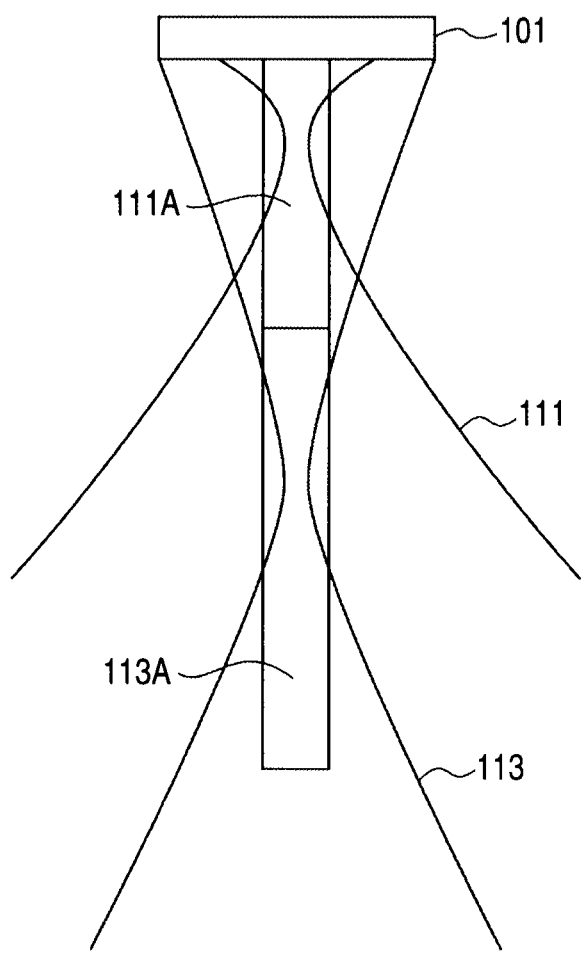
FIG. 10 is a diagram to illustrate a conception of a combination focus.
Figure 11:
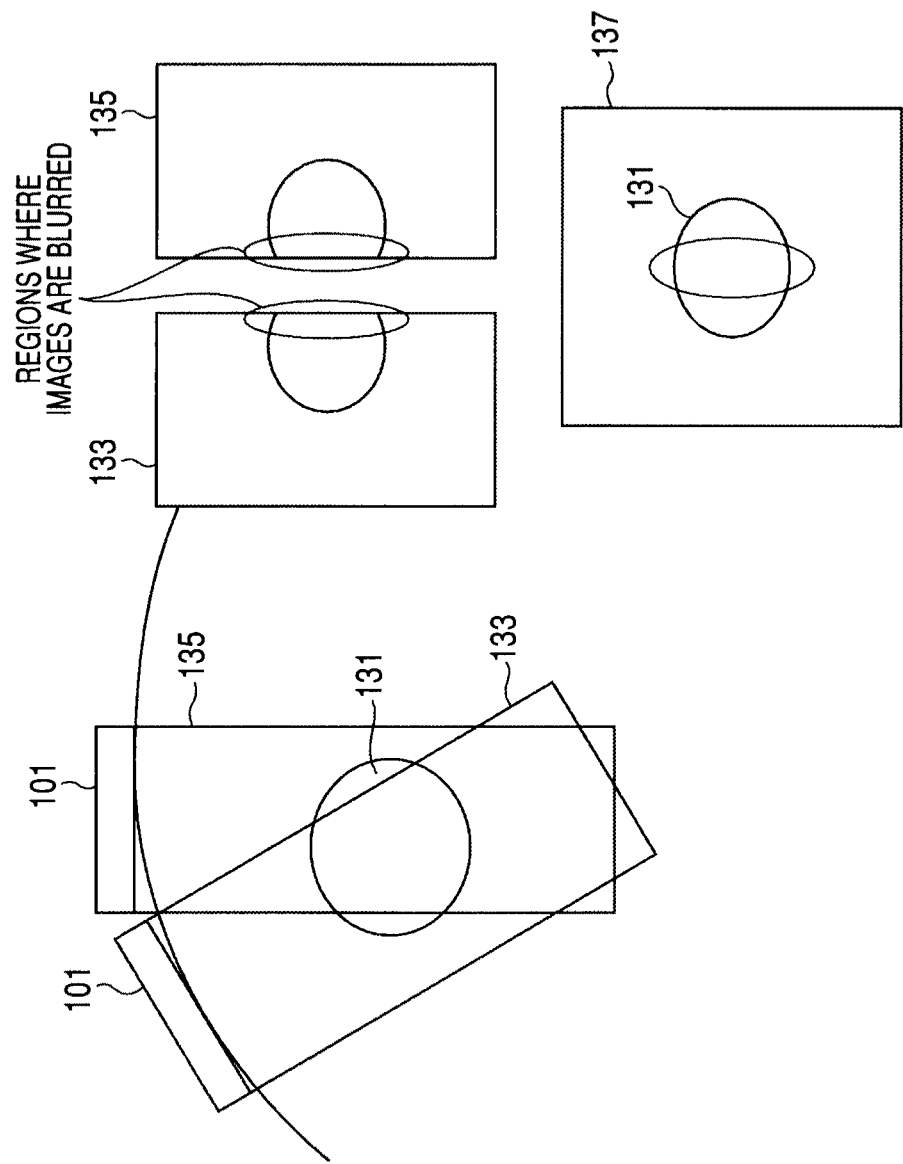
FIG. 11 is a diagram to illustrate a problem which a conventional technique has.

FIG. 7 is a diagram to illustrate a conception of a two-stage combination focus method. The borders of the image 51A obtained by the ultrasound beam 51 of a short-distance focus and the image 53A obtained by the ultrasound beam 53 of a long-distance focus overlap to generate the overlap region 55A, and the synthesis processing described in the one embodiment is performed for the overlap region 55A.

With this, increase of the resolving power or reduction of speckles in the image after the synthesis processing can be expected. In this case, the order of the processing by the image synthesizing unit 14 and the processing by the coordinate converting unit 12 may be reversible.

Eighth Modified Example

The one embodiment is applicable to the synthesis processing by the frequency compound scan. In addition, a synthesis processing of an image of a fundamental frequency and an image of second-order harmonics is a kind of the frequency compound as well. According to the frequency compound scan, respective scan ranges are matched, so the one embodiment is applicable in the same manner as the combination focus method.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasound diagnosis apparatus for performing an ultrasound scan multiple times such that the same region of a subject overlaps in at least a portion and for generating images of a plurality of frames based on a received echo, the ultrasound diagnosis apparatus comprising:
   an analyzing unit configured to perform a multiple resolution analysis for the generated images by wavelet transform;
   a filter operation processing unit configured to perform a filter operation processing for each of wavelet coefficients corresponding among the images of a plurality of frames, in each wavelet coefficient of each resolution obtained by the multiple resolution analysis by the analyzing unit; and
   an image generating unit configured to perform wavelet inverse transform of the predetermined transform processing for a result of the filter operation processing by the filter operation processing unit, to generate an image of one frame,
   wherein the filter operation processing performed for each of the wavelet coefficients uses, for each pixel among the images of a plurality of frame, a wavelet coefficient for said each pixel and a wavelet coefficient for at least one adjacent pixel within a predetermined distance, and the filter operation processing unit is configured to take a mean value for wavelet coefficients at a relatively low frequency side and to output a larger absolute value for wavelet coefficients at a relatively high frequency side, of the wavelet coefficients obtained by the multiple resolution analysis.

2. The ultrasound diagnosis apparatus according to claim 1, wherein the filter operation processing by the filter operation processing unit is an operation processing to output a larger absolute value for all the wavelet coefficients.

3. The ultrasound diagnosis apparatus according to claim 1, further comprising an edge component removing unit configured to remove an edge component generated resulting from the wavelet transform by the analyzing unit, at edges of mutually overlapping regions among the images of a plurality of frames, after performing the multiple resolution analysis by the analyzing unit and before performing the filter operation processing by the filter operation processing unit.

4. The ultrasound diagnosis apparatus according to claim 1, further comprising a non-linear diffusion filter processing unit configured to perform a non-linear diffusion filter processing for the respective images before and/or after performing the filter operation processing by the filter operation processing unit.

5. The ultrasound diagnosis apparatus according to claim 1, further comprising an image processing unit configured to multiply each wavelet coefficient after the filter operation processing by a predetermined coefficient, before performing the wavelet inverse transform by the image generating unit.

6. The ultrasound diagnosis apparatus according to claim 1, further comprising a coordinate converting unit configured to coordinate-convert the images into a display coordinate for display on a predetermined display unit,
   wherein the processings by the analyzing unit, the filter operation processing unit and the image generating unit are performed before the coordinate-conversion processing or after the coordinate-conversion processing by the coordinate converting unit.

7. The ultrasound diagnosis apparatus according to claim 6, wherein the ultrasound scan comprises:
   a scan for performing transmission/reception of ultrasound beam from a plurality of different directions with respect to the same portion of a subject;
   a scan for obtaining the images while moving an ultrasound probe on a subject and for detecting a motion of the ultrasound probe based on the obtained images to perform a position-fitting of the images;
   a scan for performing a three-dimensional scan from a plurality of different directions with respect to the same portion of a subject;
   a scan for performing transmission/reception of ultrasound beam multiple times from the same direction with respect to a subject while varying a transmitting frequency and/or a receiving frequency of the ultrasound beam; and
   a scan for performing transmission/reception of ultrasound beam multiple times from the same direction with respect to a subject while varying a transmitting focus.

8. A non-transitory computer readable storage medium storing a program which when executed by a computer causes the computer to perform ultrasound imaging steps in regard to return echo signals produced by an ultrasound diagnosis apparatus performing an ultrasound scan multiple times such that the same region of a subject overlaps in at least a portion, said imaging steps generating images of a plurality of frames based on a received echo and comprising:
   an analyzing step configured to perform a multiple resolution analysis for the generated images of a plurality of frames by wavelet transform;
   a filter operation step configured to perform a filter operation processing for each of the coefficients corresponding among the images of a plurality of frames, in each coefficient of each resolution obtained by the performed multiple resolution analysis; and
   an image generating step configured to perform an inverse transform processing of the predetermined transform processing for a result of the filter operation processing by the filter operation processing, to generate an image of one frame,
   wherein the filter operation step for each of the wavelet coefficients is configured to use, for each pixel among the images of a plurality of frame, a wavelet coefficient for said each pixel and a wavelet coefficient for at least one adjacent pixel within a predetermined distance, and to take a mean value for wavelet coefficients at a relatively low frequency side and to output a larger absolute value for wavelet coefficients at a relatively high frequency side, of the wavelet coefficients obtained by the multiple resolution analysis.

9. The non-transitory computer readable storage medium according to claim 8, wherein the filter operation processing by the filter operation processing step is an operation processing to output a larger absolute value for all the wavelet coefficients.

10. The non-transitory computer readable storage medium according to claim 8, storing a further imaging step comprising an edge component removing step configured to remove an edge component generated resulting from the wavelet transform by the analyzing step, at edges of mutually overlapping regions among the images of a plurality of frames, after performing the multiple resolution analysis by the analyzing step and before performing the filter operation processing by the filter operation processing step.

11. The non-transitory computer readable storage medium according to claim 8, storing a further imaging step comprising a non-linear diffusion filter processing step configured to perform a non-linear diffusion filter processing for the respective images before and/or after performing the filter operation processing by the filter operation processing step.

12. The non-transitory computer readable storage medium according to claim 8, storing a further imaging step comprising an image processing step configured to multiply each wavelet coefficient after the filter operation processing by a predetermined coefficient, before performing the wavelet inverse transform by the image generating step.

13. The non-transitory computer readable storage medium according to claim 8, storing a further imaging step comprising a coordinate converting step configured to coordinate-convert the images into a display coordinate for display on a predetermined display unit, wherein the processings by the analyzing step, the filter operation processing step and the image generating step are performed before the coordinate-conversion processing or after the coordinate-conversion processing by the coordinate converting step.

14. The non-transitory computer readable storage medium according to claim 8, wherein the ultrasound scan comprises:
a scan for performing transmission/reception of ultrasound beam from a plurality of different directions with respect to the same portion of a subject;
a scan for obtaining the images while moving an ultrasound probe on a subject and for detecting a motion of the ultrasound probe based on the obtained images to perform a position-fitting of the images;
a scan for performing a three-dimensional scan from a plurality of different directions with respect to the same portion of a subject;
a scan for performing transmission/reception of ultrasound beam multiple times from the same direction with respect to a subject while varying a transmitting frequency and/or a receiving frequency of the ultrasound beam; and
a scan for performing transmission/reception of ultrasound beam multiple times from the same direction with respect to a subject while varying a transmitting focus.

* * * * *